(12) United States Patent
Gall (10) Patent No.: US 8,069,858 B2
(45) Date of Patent: Dec. 6, 2011

(54) METHOD AND APPARATUS FOR DEPLOYING A SHAPE MEMORY POLYMER

(75) Inventor: Kenneth A. Gall, Atlanta, GA (US)

(73) Assignee: Medshape Solutions, Inc., Atlanta, GA (US)

( * ) Notice: Subject to any disclaimer, the term of this patent is extended or adjusted under 35 U.S.C. 154(b) by 0 days.

(21) Appl. No.: 12/960,276

(22) Filed: Dec. 3, 2010

(65) Prior Publication Data

US 2011/0067712 A1    Mar. 24, 2011

Related U.S. Application Data

(63) Continuation of application No. PCT/US2008/071066, filed on Jul. 24, 2008.

(51) Int. Cl.
*A61B 19/00*    (2006.01)

(52) U.S. Cl. ................................................ 128/898

(58) Field of Classification Search .......... 623/1.11–1.2, 623/1.23, 1.32, 1.44–1.4, 1.49; 606/72–78, 606/151–157; 264/230–234
See application file for complete search history.

(56) References Cited

U.S. PATENT DOCUMENTS

| | | | |
|---|---|---|---|
| 4,950,258 A | 8/1990 | Kawai et al. | |
| 5,002,563 A | 3/1991 | Pyka et al. | |
| 5,163,952 A | 11/1992 | Froix | |
| 5,358,511 A | 10/1994 | Gatturna et al. | |
| 5,601,557 A | 2/1997 | Hayhurst | |
| 5,676,175 A * | 10/1997 | Bar et al. .................. | 138/97 |
| 5,779,707 A | 7/1998 | Bertholet et al. | |
| 5,964,744 A | 10/1999 | Balbierz | |
| 6,113,611 A | 9/2000 | Allen et al. | |
| 6,160,084 A | 12/2000 | Langer et al. | |
| 6,281,262 B1 | 8/2001 | Shikinami | |
| 6,388,043 B1 | 5/2002 | Langer et al. | |
| 6,500,204 B1 | 12/2002 | Igaki | |
| 6,579,305 B1 * | 6/2003 | Lashinski .................. | 623/1.11 |
| 6,637,995 B1 | 10/2003 | White | |
| 6,663,664 B1 * | 12/2003 | Pacetti .................. | 623/1.2 |
| 6,702,976 B2 | 3/2004 | Sokolowski | |
| 6,720,402 B2 | 4/2004 | Langer et al. | |
| 7,151,157 B2 | 12/2006 | Mather | |
| 7,303,642 B2 | 12/2007 | Topolkaraev | |

(Continued)

FOREIGN PATENT DOCUMENTS

EP    0368274    5/1990

(Continued)

OTHER PUBLICATIONS

International Search Report from PCT Application No. PCT/US06/15207 (Aug. 18, 2006).

(Continued)

*Primary Examiner* — William H. Matthews
(74) *Attorney, Agent, or Firm* — Greeberg Traurig, LLP (57) ABSTRACT

Methods and apparatus described herein may utilize activation of an SMP material to install medical devices with respect to a surgical site. Activation of the SMP material may be performed with the use of a triggering force and/or a constraint applied to the SMP material. Activation using a triggering force and/or a constraint may be used to create varied activation rates in an SMP material and may be combined with temperature or other activation stimuli to create the varied activation rates.

6 Claims, 8 Drawing Sheets

U.S. PATENT DOCUMENTS

| | | | |
|---|---|---|---|
| 7,556,647 | B2 | 7/2009 | Drews et al. |
| 7,632,303 | B1 | 12/2009 | Stalker et al. |
| 7,651,528 | B2 | 1/2010 | Montgomery et al. |
| 2002/0062547 | A1 | 5/2002 | Chiodo et al. |
| 2003/0055198 | A1 | 3/2003 | Langer et al. |
| 2003/0191276 | A1 | 10/2003 | Lendlein et al. |
| 2003/0208211 | A1* | 11/2003 | Kortenbach .................. 606/151 |
| 2004/0014929 | A1 | 1/2004 | Lendlein et al. |
| 2004/0024143 | A1 | 2/2004 | Lendlein et al. |
| 2004/0068262 | A1 | 4/2004 | Lemos et al. |
| 2004/0073256 | A1 | 4/2004 | Marchitto et al. |
| 2004/0098110 | A1 | 5/2004 | Williams et al. |
| 2004/0110285 | A1 | 6/2004 | Lendlein et al. |
| 2004/0117955 | A1 | 6/2004 | Barvosa-Carter et al. |
| 2004/0260298 | A1 | 12/2004 | Kaiser et al. |
| 2005/0033295 | A1 | 2/2005 | Wisnewski |
| 2005/0090822 | A1 | 4/2005 | DiPoto |
| 2005/0244353 | A1 | 11/2005 | Lendlein et al. |
| 2006/0009785 | A1 | 1/2006 | Maitland et al. |
| 2006/0036045 | A1 | 2/2006 | Wilson et al. |
| 2006/0041089 | A1 | 2/2006 | Mather et al. |
| 2007/0073293 | A1 | 3/2007 | Martz et al. |
| 2008/0141736 | A1 | 6/2008 | Jones et al. |
| 2008/0228186 | A1 | 9/2008 | Gall et al. |
| 2009/0005777 | A1 | 1/2009 | Houser et al. |
| 2009/0118747 | A1 | 5/2009 | Bettuchi et al. |
| 2009/0222025 | A1 | 9/2009 | Catanese, III et al. |
| 2009/0248141 | A1 | 10/2009 | Shandas |
| 2009/0306767 | A1 | 12/2009 | Lendlein |
| 2010/0152735 | A1 | 6/2010 | Brown et al. |

FOREIGN PATENT DOCUMENTS

| | | |
|---|---|---|
| EP | 0668055 | 8/1995 |
| EP | 1481640 | 12/2004 |
| EP | 1607048 | 12/2005 |
| JP | 2003145564 | 5/2003 |
| WO | WO 92/13490 | 8/1992 |
| WO | WO 96/11721 | 4/1996 |
| WO | WO 2004/014217 | 2/2004 |
| WO | WO 2006/108114 | 10/2006 |
| WO | WO 2007/038429 | 4/2007 |
| WO | WO 2007/089843 | 8/2007 |
| WO | WO 2008/034277 | 3/2008 |
| WO | WO 2008/051254 | 5/2008 |
| WO | WO 2008/129241 | 10/2008 |
| WO | WO 2009/050717 | 4/2009 |
| WO | WO 2009/105663 | 8/2009 |
| WO | WO 2009/132284 | 10/2009 |

OTHER PUBLICATIONS

International Search Report and Written Opinion in PCT Application No. PCT/US08/058249 (Jul. 22, 2008).

International Search Report and Written Opinion in PCT Application No. PCT/US08/071066 (Jul. 24, 2009).

Bellin et al., *Polymeric triple-shape materials*, 103 Proc. Nat'l Acad. Sci. U.S.A. (PNAS), 18043-18047 (2006).

Diani et al., *Finite Strain 3D Thermoviscoelastic Constitutive Model for Shape Memory Polymers*, 42 Polymer Engineering and Science, 486-492 (2006).

El Feninat et al., *Shape Memory Materials for Biomedical Applications*, Advanced Engineering Materials, 4, No. 3, pp. 91-104 (2007).

Franzesi, *Design of a novel anterior cruciate ligament prosthesis*, Massachusetts Institute of Technology Thesis (2006), http://hdl.handle.net/1721.1/36693.

Gall et al., *Thermomechanics of the Shape Memory Effect in Polymers for Biomedical Applications*, Wiley InterScience, pp. 339-348 (2005).

Gall et al., *Shape-Memory Polymers for Microelectromechanical Systems*, Journal of Microelectromechanical Systems, vol. 13, No. 3, pp. 472-483 (Jun. 2004).

Gall et al., *Shape Memory Polymer Nanocomposites*, Acta Materialia 50, pp. 5115-5126 (2002).

Jeon et al., *Shape Memory and Nanostructure in Poly(Norbornyl-POSS) Copolymers*, Polymers International, 49, pp. 453-457 (2000).

Langer et al., *Designing Materials for Biology and Medicine*, Nature, vol. 428, pp. 487-492 (Apr. 1, 2004).

Lendlein et al., *Shape-memory polymers as stimuli-sensitive implant materials*, 32 Clinical Hemorheology and Microcirculation 105-116 (2005).

Lendlein et al., *Light-Induced Shape-Memory Polymers*, Nature, vol. 434, pp. 879-882 (Apr. 14, 2005).

Lendlein et al., *Biodegradable, Elastic Shape-Memory Polymers for Potential Biomedical Applications*, Science, vol. 296, pp. 1673-1676 (May 31, 2002).

Lendlein et al., *AB-Polymer Networks Based on Oligo(Varepsilon-Caprolactone) Segments Showing Shape-Memory Properties*, Proceedings of the National Academy of Sciences of the United States of America, vol. 98, No. 3, pp. 842-847 (Jan. 30, 2001).

Lin et al., *Study on Shape-Memory Behavior of Polyether-Based Polyurethanes. I. Influence of the Hard-Segment Content*, Journal of Applied Polymer Science, vol. 69, pp. 1563-1574 (1998).

Lin et al., *Study on Shape-Memory Behavior of Polyether-Based Polyurethanes. II Influence of the Soft-Segment Molecular Weight*, Journal of Applied Polymer Science, vol. 69, pp. 1575-1586 (1998).

Liu et al., *Thermomechanics of Shape Memory Polymers: Uniaxial Experiments and Constitutive Modeling*, International Journal of Plasticity, vol. 22, pp. 279-313 (2006).

Liu et al., *Thermomechanical Recovery Couplings of Shape memory Polymers in Flexure*, Smart Materials and Structures, vol. 12, pp. 947-954 (2003).

Liu et al., *Chemically Cross-Linked Polycyclooctene Jul. 28, 2008 Synthesis, Characterization, and Shape Memory Behavior*, Macromolecules, vol. 35, No. 27, pp. 9868-9874 (2002).

Maitland et al., *Photothermal Properties of Shape Memory Polymer Micro-Actuators for Treating Stroke*, Lasers in Surgery and Medicine, vol. 30, pp. 1-11 (2002).

Metcalfe et al., *Cold Hibernated Elastic Memory Foams for Endovascular Interventions*, Biomaterials, vol. 24, pp. 491-497 (2003).

Metzger et al., *Mechanical Properties of Mechanical Actuator for Treating Ischemic Stroke*, Biomedical Microdevices, vol. 4, No. 2, pp. 89-96 (2002).

Rupp et al., *Resulting Tensile Forces in the Human Bone-Patellar Tendon-Bone Graft: Direct Force Measurement in Vitro*, Arthroscopy: The Journal of Arthroscopic and Related Surgery, vol. 15, No. 2, pp. 179-184 (Mar. 1999).

Smith, T., *Strength of Elastomers—A Perspective*, Polymer Engineering and Science, vol. 17, No. 3, pp. 129-143 (Mar. 1977).

Smith, T., *Time and Temperature Dependence of the Ultimate Properties of an SBR Rubber at Constant Elongations*, Journal of Applied Physics, vol. 31, No. 11, pp. 1892-1898 (Nov. 1960).

Smith, T., *Ultimate Tensile Properties of Elastomers. I. Characterization by a Time and Temperature Independent Failure Envelope*, Journal of Polymer Science, Part A, vol. 1, No. 12, pp. 3597-3616 (Dec. 1963).

Sokolowski et al., *Cold Hibernated Elastic Memory (CHEM) self-deployable structures*, SPIE '99 International Symposium on Smart Structures and Materials (1999).

Sokolowski et al., *Medical Applications of shape memory polymers*, 2 Biomedical Materials S23-S27 (2007).

Takahashi et al., *Structure and Properties of Shape-Memory Polyurethane Block Copolymers*, Journal of Applied Polymer Science, vol. 60, pp. 1061-1069 (1996).

Tobushi et al., *Thermomechanical Constitutive Modeling in Shape Memory Polymer of Polyurethane Series*, Journal of Intelligent Material Systems and Structures, vol. 8, pp. 711-718 (Aug. 1997).

Tobushi et al., *Thermomechanical Properties in a Thin Film of Shape Memory Polymer of Polyurethan Series*, Smart Matter Structures, vol. 5, pp. 483-491 (1996).

Wache et al., *Development of a Polymer Stent with Shape Memory Effect as a Drug Delivery System*, Journal of Materials Science: Materials in Medicine, vol. 14, pp. 109-112 (2003).

Yakacki et al., *Strong and Biocompatible Shape Memory Polymers for Soft Tissue Orthopedic Fixation*, Submitted to Nature Materials (2006).

Yakacki et al., *Unconstrained recovery characterization of shape-memory polymer networks for cardiovascular applications*, 28 Biomaterials 2255-2263 (2007).

Yakacki et al., *Deformation Limits in Shape-Memory Polymers*, 10 Advanced Engineering Materials 112-119 (2008).

Zhu et al., *Shape-Memory Effects of Radiation Crosslinked Poly($\epsilon$-Caprolactone)*, Journal of Applied Polymer Science, vol. 90, pp. 1589-1595 (2005).

\* cited by examiner

METHOD AND APPARATUS FOR DEPLOYING A SHAPE MEMORY POLYMER

RELATED APPLICATIONS

This application is a continuation under 35 U.S.C. §120 of International Application No. PCT/US2008/071066, filed Jul. 24, 2008, entitled "Method and Apparatus for Deploying A Shape Memory Polymer."

BACKGROUND

Medical personnel use a variety of implantable medical devices in a patient to position, fix, hold, and otherwise manipulate a patient's body. The installation procedures for such implantable medical devices may be advantageously designed to allow medical personnel to install the medical device quickly, effectively, and consistently. The design of the medical device may actually facilitate and/or simplify the installation procedure. Furthermore, the design of a medical device may facilitate a particular installation procedure. Active elements of a medical device, including shape memory polymer portions, may be incorporated in medical devices. A shape memory polymer (SMP) may be activated to induce shape change and/or to generate forces against constraints surrounding the SMP. Medical devices comprising SMP portions may utilize activation of the SMP portion to change the configuration of the medical device to an installed configuration with respect to a surgical site and/or to generate forces against the surgical site.

SUMMARY

Methods and apparatus described herein may utilize activation of an SMP material to install medical devices with respect to a surgical site. Activation of the SMP material may be performed with the use of a triggering force and/or a constraint applied to the SMP material. Activation using a triggering force and/or a constraint may be used to create varied activation rates in an SMP material and may be combined with temperature or other activation stimuli to create the varied activation rates.

The disclosure describes an exemplary method that includes inserting into a surgical site a medical device including a shape memory polymer portion having a stored strain. The method also includes raising the temperature of the shape memory polymer portion to a first activation temperature, thereby activating the shape memory polymer portion at a first activation rate. The method also includes applying a trigger force to the shape memory polymer portion, thereby changing the activation rate of the shape memory polymer portion from the first activation rate to a second activation rate.

The disclosure also describes an exemplary method that includes straining a shape memory polymer that forms at least a portion of a medical device with a deforming force from an unconstrained shape to a pre-implantation shape. The method also includes inserting the medical device into a surgical site while the shape memory polymer is in the pre-implantation shape. The method also includes applying a trigger force to the shape memory polymer, thereby activating the shape memory polymer, and reducing the trigger force after the shape memory polymer has achieved a post-implantation shape different from the pre-implantation shape.

The disclosure also describes an exemplary medical device that includes a body having a shape memory polymer portion, with the shape memory polymer portion in a storage shape having a stored strain. The stored strain corresponds to a first difference in length between a first unconstrained length of the shape memory polymer portion in an unconstrained shape and a first storage length of the shape memory polymer portion in the storage shape, with each first length being measured along a first measured direction of the shape memory polymer portion. The medical device also includes a trigger element adapted to be coupled with the body, the trigger element being further adapted to activate the shape memory polymer portion while the shape memory polymer portion is in the storage shape. The trigger element is adapted to activate the shape memory polymer portion through application of a trigger force to the shape memory polymer portion.

The disclosure also describes an exemplary medical device including an elongated body having a shape memory polymer portion having a stored strain. The medical device also includes a trigger element oriented with respect to the elongated body such that a displacement of the trigger element transfers an installation strain to the shape memory polymer portion.

DETAILED DESCRIPTION

The following description of various embodiments is merely exemplary in nature. While various embodiments have been described for purposes of this specification, various changes and modifications may be made to the embodiments disclosed herein.

A polymer having a shape memory property, which may be termed a "shape memory polymer" (SMP), may be characterized by an ability to retain a "memory" of a shape in as much as the SMP may change shape and return to the memorized shape under a certain set of conditions through a process of activation, described further herein. As used herein, "SMP" may refer to a body or a portion of a body that has an SMP property The memorized shape is also referred to herein as an unconstrained shape of the SMP because the SMP may achieve the memorized shape in the absence of constraints and after all stored strain in the SMP is recovered. The term "stored strain" as used herein is the strain defined by the difference between the unconstrained shape and a storage shape, also referred to herein as a temporary shape. In other words, a material may have an inhomogeneous stored strain comprising multiple regions with strains that differ from one another.

As used herein, the term "strain" (when used without a qualifier) is used to refer to an engineering strain in the form of a linear/normal strain, a shear strain, and/or any combination thereof in a material. Linear strain (or normal strain) is the difference in length (e.g., distortion) of a material along a measured direction divided by the original length of that material along the measured direction. The "measured direction" of the linear strain may referred to herein simply as the direction of the linear strain. The difference in length is measured by the new length subtracted by the original length. Therefore, negative strains indicate compression along the measured direction and positive strains indicate expansion along the measured direction. Shear strain is the differential angular change in a line through a body between a reference point and a point that moves based on deformation. Strains are associated with measured directions and/or lines through the material and are dimensionless. Complex distortions and shape changes in a material (e.g., SMP) may include multiple types and directions of strain such as one or more linear strains and/or shear strains. For example, a bend in a material may comprise one or more concurrent linear strains (e.g., areas of compression and/or expansion) along one or more measured directions. As another example, a twist in a material may comprise one or more shear strains (e.g., angular distortions).

An SMP may be caused to take on a temporary shape different from the memorized shape through straining the SMP from the memorized (unconstrained) shape to the storage (temporary) shape. This process of straining the SMP from a memorized to a storage shape may also be referred to herein as "deforming" the SMP or "setting a temporary shape". The strain imparted to an SMP that is necessary to set the temporary shape in the SMP may be incrementally different from the stored strain eventually held by the SMP in the temporary shape. For example, during the setting of the temporary shape, if a force is reduced/removed from the SMP, the SMP may recoil from the imparted strain into the stored strain embodied in the temporary shape.

Under conditions where an SMP is not activated, the SMP will maintain a temporary shape and the molecules of the SMP will maintain a lower entropy state (e.g., configuration of the molecules) than the state of the molecules while the SMP is in the unconstrained shape. When an SMP is activated, the molecules of the SMP are allowed to seek a higher entropy state and when the SMP is not activated, the molecules of the SMP are limited from seeking a higher entropy state. The term "activation," as used herein, refers to enabling recovery in an SMP through providing activation stimuli to the SMP, and thereby inducing the molecules to seek a higher entropy configuration. Depending on the constraints applied to the SMP material, recovery caused by activation can include shape change and/or generation of forces against a constraint. For example, even though activation may enable a change in molecular configuration (and thereby a shape change), that shape change may be inhibited by the application of external constraints.

In accordance with the present disclosure, methods and apparatus have been developed whereby mechanical stimuli may be used as activating stimuli for an SMP. Mechanical stimuli may be referred to as a force and/or a constraint applied to the SMP material. For different activation stimuli, such as temperature and/or trigger forces, as described further herein, different "activation rates" are may be achieved. Different activation rates may be measured through the externally-observable properties of an SMP, including shape change and generation of force, as described further herein.

The term "constraint" as used herein refers to a structural confinement (limitation in one or more directions) on a body. A constraint may or may not have forces generated against it by the body. A constraint applied to an SMP may be used as an externally measurable indication of a trigger force applied to the SMP. For example, a trigger force may not be easily measurable, so the application of a constraint or a series of constraints may be used to control the activation of an SMP. As described further herein, the application of a constraint on an SMP may cause a varying force on the SMP as the SMP responds to the applied constraint, through the SMP responding elastically and/or the SMP responding with conformational motion. For example, the application of a constraint may cause a sufficient force to be applied to the SMP such that a yield point is crossed and conformational motion of the SMP molecules occurs, thereby conforming the SMP to the constraint and lowering the force applied by the constraint. As described further herein, the application of a series of constraints may raise and lower through multiple cycles the forces applied on the SMP by the series of constraints.

An activation temperature of an SMP is a temperature above which the SMP is significantly activated (e.g., which causes significant recovery in the SMP) absent other activation stimuli. Activation temperatures and other transition temperatures for SMPs may be defined by changes in macroscopic material properties, such as changes in the modulus of the SMP (e.g., an inflection point in a modulus curve, a midpoint of a transition in a modulus curve). The modulus of an SMP may be measured using standard techniques known to those with skill in the art, such as through using a dynamic modulus analysis setup. An SMP need not reach or exceed its so-called "transition temperature" for activation to occur. For example, activation of an SMP may occur in a temperature range below the transition temperature of the SMP.

In an SMP material with a high cross-linking density, the activation temperature may be about 30-20 degrees Celsius below the transition temperature and the SMP material may be designated as having a broad transition (e.g., a broad range of temperatures in which recovery significantly occurs). In an SMP material with a moderate cross-linking density, the activation temperature may be about 20-10 degrees Celsius below the transition temperature and the SMP material may be designated as having a moderate transition. In an SMP material with a low cross-linking density, the activation temperature may be about ten to three degrees Celsius below the transition temperature and the SMP material may be designated as having a narrow transition. In an SMP material with a very low cross-linking density, the activation temperature may be about 3 or fewer degrees Celsius below the transition temperature and the SMP material may be designated as having a very narrow transition.

An unconstrained shape refers to a shape of an SMP portion with no strain that has been imparted or stored. An unconstrained shape may be achieved through full activation (e.g., release of all stored strain) such as through sufficient activation in an unconstrained environment. An unconstrained environment may be any environment with little or no constraints imposed on the SMP material, such as the SMP material submerged in a fluid bath or resting on a table.

Activation rates may be tested or benchmarked in an unconstrained environment given predetermined activating stimuli as described further herein (e.g., temperature, trigger force) applied to a test sample of the SMP material. For example, a test activation rate may be determined through applying a predetermined temperature (e.g., temperature controlled fluid bath) to the sample of SMP material (with a stored strain) in an unconstrained environment and measuring the strain recovery (shape change) that occurs over time. For example, a first exemplary test or benchmark activation rate may be determined to be five percent strain recovery in 30 minutes. A second exemplary test or benchmark activation rate may be five percent strain recovery in 15 minutes. A third exemplary test or benchmark activation rate may be five percent strain recovery in ten minutes. A fourth exemplary test or benchmark activation rate may be five percent strain recovery in five minutes. A fifth exemplary test or benchmark activation rate may be 20 percent strain recovery in 15 minutes. A sixth exemplary test or benchmark activation rate may be 20 percent strain recovery in ten minutes. Other test or benchmark rates as selected based on an appropriate rate for the surgical procedure. The activation rates as measured by percentage recovery over a certain period of time may be extrapolated to larger or smaller strain recoveries, and actual activations and recoveries are not limited to the specific percentages or time periods described herein. For example, recoveries of less than one percent strain to greater than 100 percent strain (e.g., in the case of tensile strain) may be recovered by shape memory polymers.

As described further herein, different activation rates may be achieved through application of trigger forces. Activation rates may also be controlled/changed through the modification of temperature and/or trigger forces or combinations thereof during surgical procedures using the devices described herein.

The discussion herein of activation rates should be understood as including long-term (e.g., average) activation rates, as well as instantaneous activation rates. The activation rates described herein may be changed through changes in stimuli (e.g., forces, temperature) causing the activation. For example, an activation rate may vary considerably within a large range during activation during a surgical procedure. The activation rate of the SMP may therefore be equal to each of the values in that range for a period of time, however short.

Stored strains and triggering forces may be compressive, expansive, bending, torsional and/or any combination of those forces/strains. In order for a force or a constraint to trigger activation of an SMP material, the force or constraint may have at least a component that bears a certain relation(s) to the stored strain in the SMP. Some embodiments of trigger forces or constraints may have components perpendicular to the stored strain. Some embodiments of triggering forces/constraints may have components in an opposite and parallel direction to the stored strain. The term "parallel" is used herein to describe a relationship such that two vectors (e.g., relating to two forces, relating to two strains) share the same direction, and may or may not be translated (e.g., have a different initial point). For example, two forces or vectors directly opposing each other are parallel.

The term "trigger force" is used herein to denote a force exerted on the SMP body that causes activation of the SMP (e.g., an increase in activation rate), as described further herein. The trigger force may be transmitted through other parts of a medical device to an SMP portion. As an example, the medical device may be constructed entirely from SMP material or may include other materials that are not SMP materials. In one embodiment, the SMP subjected to the trigger force may receive the trigger force through these other materials. In another embodiment, the SMP subjected to the trigger force may receive the trigger force through a portion of SMP that does not activate due to the application of the trigger force. As examples, the SMP that does not activate may not have any stored strain or may not have a stored strain that is activated by the particular direction of the trigger force being applied.

A "trigger element" may be adapted, as described further herein, to apply trigger force(s) and/or constraint(s) on an SMP material in order to activate the SMP material. For example, an element may be adapted to apply compressive force(s) and constraint(s) in a perpendicular direction to a stored compressive strain (e.g., negative strain along a measured direction) in the SMP material. As another example, a trigger element may be adapted to apply expansive forces and/or constraints in a parallel direction to a stored compressive strain in the SMP material. As a further example, a trigger element may be adapted to apply a trigger force or constraint in a rotational or bending direction that is opposite a rotational or bending direction of a stored strain (e.g., a strain with a shear component).

Implantable medical devices described herein use various shapes SMP portions and transitions between those shapes to achieve advantageous configurations. The medical device configurations may be advantageously applied with respect to bone, soft tissue, and other elements in a surgical site. The medical device configurations may interact with these elements in the surgical site through various equilibria reached between the medical device and these elements and the respective strains embodied in these elements.

The term "surgical site" as used herein may include any portion of a patient to which operating personnel (e.g., surgeon, nurse) may have access during surgery. The term "patient" as used herein should not be limited to human patients, but may include other patients as well.

Unless otherwise indicated, all numbers expressing quantities, temperatures, strains, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Figure 1:
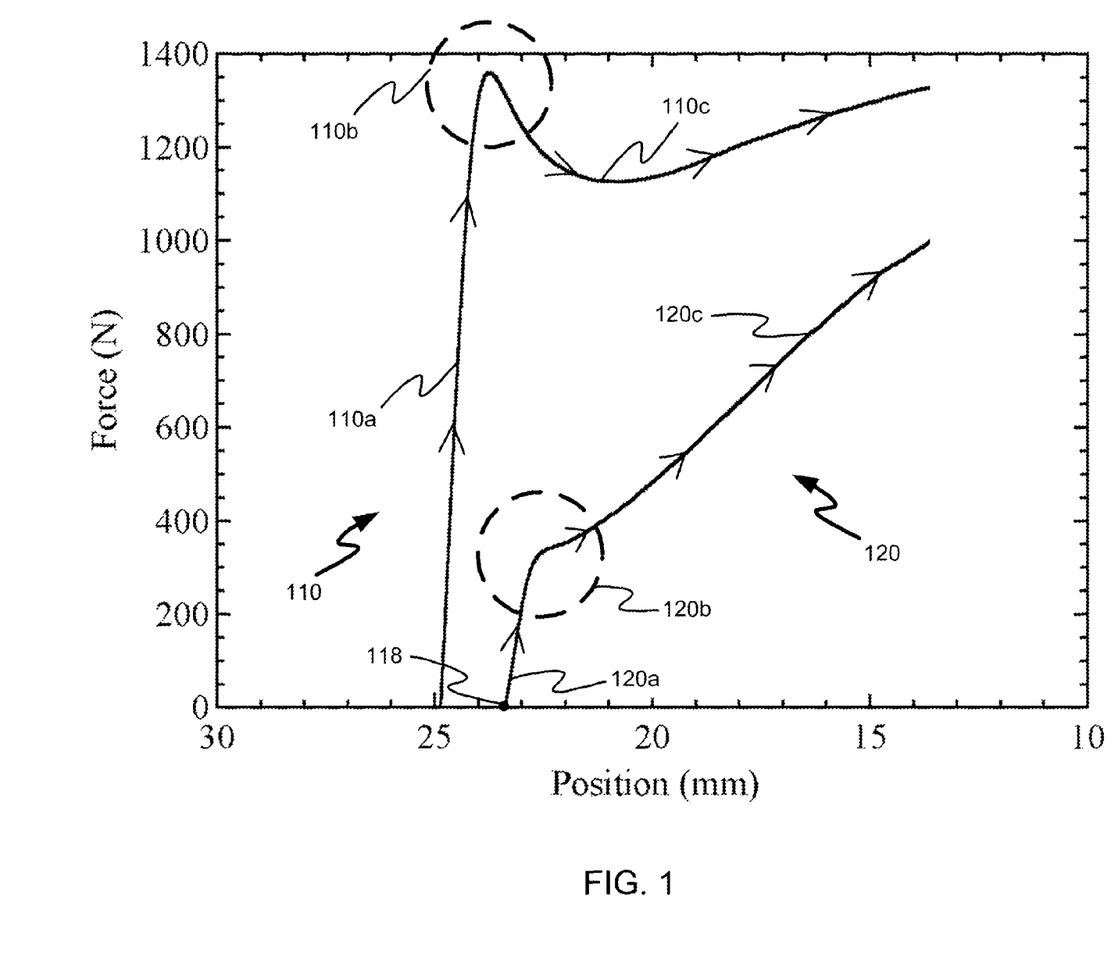
FIG. 1 is a graph of force versus displacement applied to exemplary shape memory polymer bodies with different degrees of stored strain.

FIG. 1 shows a graph of force versus displacement applied to an embodiment of a shape memory polymer. Force-displacement curve 110 tracks an embodiment of a force-displacement relationship of an SMP being deformed from an unconstrained shape into a temporary shape (e.g., imparting a stored strain) along one measured direction (in millimeters)

denoted on the displacement axis. The test elements of SMP that were used were roughly the same starting length in the measured direction, and one skilled in the art may convert the change in length along this measured direction into a strain value. The test elements shared the same cross-sectional area as measured along a plane normal to the force applied, thereby allowing equal forces to be equated to equal stresses on the test elements.

The force-displacement curve 110 begins with an initial elastic portion 110a, through a yield region 110b, continuing with a conformational motion portion 110c. After a sufficient or desired strain is imparted to the SMP through the conformational motion portion 110c, the conditions, forces and/or constraints that are imparting the strain on the SMP may be removed.

When the SMP is in a temporary shape and is not activated, the constituent molecules of the SMP are in a lower entropy configuration than when the SMP is in the unconstrained shape. The process of lowering the entropy of the configuration of molecules of the SMP occurs through a mechanism of "conformational motion" of the molecules of the SMP. An embodiment of driving the conformation motion of molecules of an SMP may be seen in the conformational motion portion 110c of the force-displacement curve 110. During the conformational motion portion 110c, a portion of the work performed on the SMP is converted into the lower entropy configuration of the molecules of the SMP.

The force-displacement curve 120 shown in FIG. 1 reflects an SMP that already has a stored strain while in initial shape with initial length 118. The force-displacement curve 120 begins with an initial elastic portion 120a. In the embodiment shown, the initial elastic portion 120a is shorter than the initial elastic portion of the force-displacement curve 110 for an SMP without a stored strain. The force-displacement curve 120 has a yield region 120b that occurs at a lower force than the yield region 110b for the SMP without stored strain. The explanation for this lowered force is that, in this embodiment, the force is applied in such a manner as to activate the SMP into releasing the stored strain.

In the embodiment shown, a conformational motion portion 120c of the force-displacement curve 120 occurs while the force is continued to be applied and as further activation occurs. The term "conformational motion" may be used to describe the process by which the configuration of the molecules changes. Conformational motion may result in raising the entropy in the molecular configuration (e.g., activation) of an SMP, shown through the conformational motion portion 120c, or may result in lowering the entropy of the molecular configuration (e.g., storing of strain, creating a temporary shape, deforming) of an SMP, shown through conformational motion portion 110c. As described further herein, conformational motion (e.g., activation, storing strain) may occur at one rate due to the temperature of the SMP, at a different rate based on mechanical forces applied to the SMP, at a different rate based on stored strain in the SMP, and at still different rates based on combinations of temperature, force, and stored strain.

During activation of an SMP portion, an activating force (e.g., a trigger force) may be a constant force and/or a varying force. In one embodiment, a constant or near-constant activating force may be applied to achieve a constant or near-constant activation rate. In another embodiment, a varying activation rate may be achieved through imposing a constraint on the SMP portion, either directly or through applying a constraint to a medical device containing the SMP portion.

For example, a constraint may be applied on the SMP portion that exerts a varying force on the SMP portion. In one embodiment, a ratchet mechanism may be applied to the SMP portion that imposes a predetermined constraint on the SMP portion whereby an incremental increase in the constraint (e.g., one notch on the ratchet mechanism) increases the force applied to the SMP portion. As the SMP portion responds to the applied constraint through conformational motion, the force applied by the ratchet mechanism decreases from a maximum magnitude force because the constraint imposed on the SMP portion remains constant while conformational motion of the SMP molecules allows the SMP to conform to the constraint. With another incremental increase in the constraint, the force applied to the SMP portion will again increase to a maximum magnitude and then decrease. Imposing constraints may be referred to herein as imposing a predetermined strain (e.g., determined by the difference between an original length and the length imposed by a stop-point in the ratchet mechanism).

While a ratchet mechanism or other mechanisms may apply discreet levels of constraint on an SMP portion, other mechanisms may be used to apply continuously variable constraints to an SMP portion. For example, there is a wide array of continuously variable mechanisms, including wedges, levers, and clamps. A continuously variable constraint may be applied to an SMP portion in order to create a constant force on the SMP portion while conformational motion is occurring. For example, a constant force may be used to activate an SMP portion at a constant or near constant rate, as described further herein. A continuously variable mechanism (e.g., wedge) may be combined with a discreet mechanism (e.g., ratchet) or discreet operation such that the continuously variable mechanism is operated in a discreet manner. For example, a wedge may be operated by a ratchet mechanism or may be operated through discreet operations (e.g., repeated impactions, hammering) such that the wedge moves in a generally discreet or incremental manner.

Figure 2:
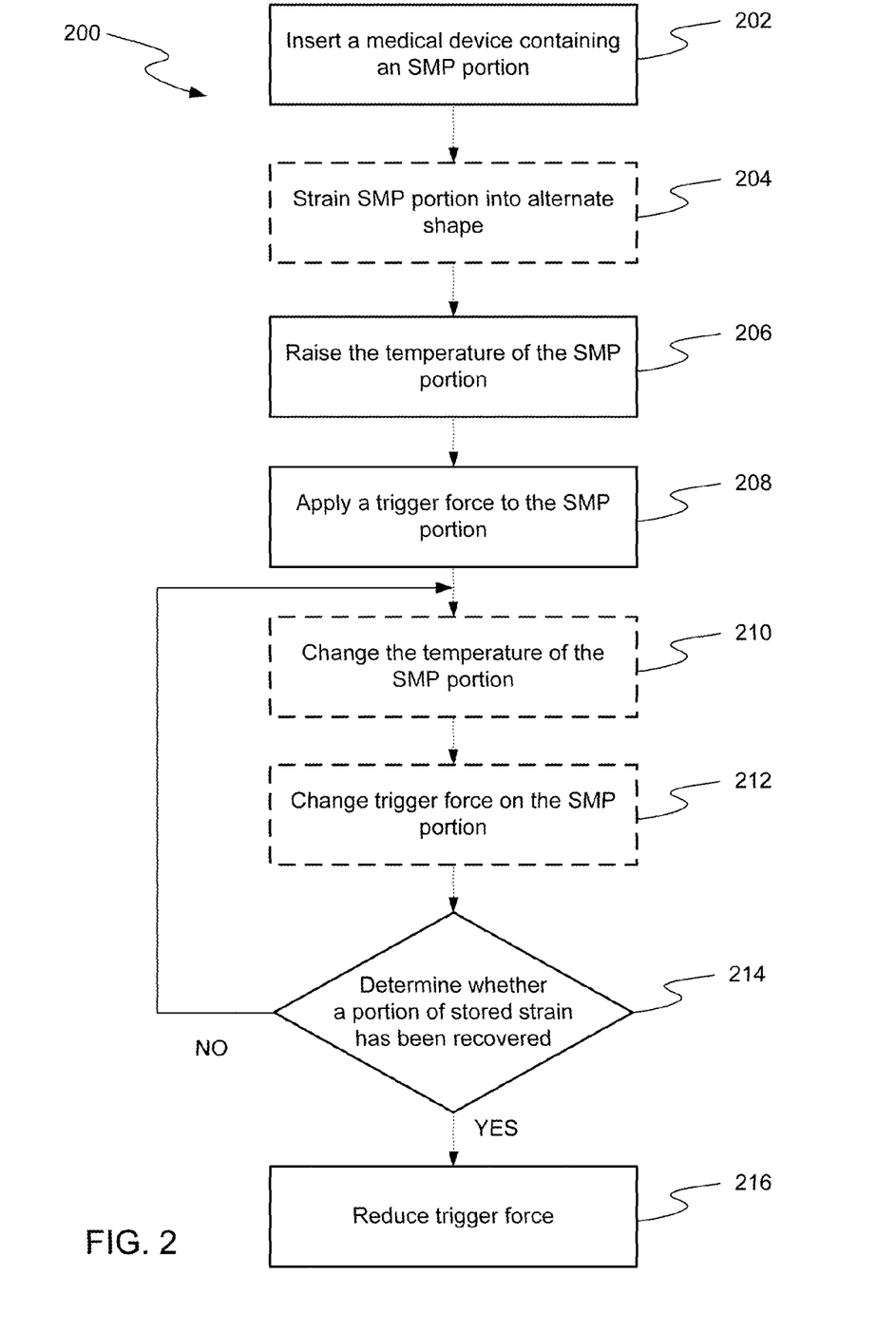
FIG. 2 is a flow chart of an exemplary method for installing a medical device having an SMP portion into a patient's body during surgery.

FIG. 2 shows a flow chart of an embodiment of a method 200 for performing surgery. The method includes inserting 202 a medical device containing an SMP portion into a surgical site. In the embodiment shown, the SMP portion of the medical device initially has a stored strain before insertion. The SMP portion with the stored strain may be referred to as being in a "temporary shape" or a "pre-implantation shape" because the shape of the SMP portion for use in the medical device is adapted for the implantation process and the SMP portion may change shape thereafter. The stored strain may be imparted by known processes for setting a temporary shape in an SMP.

In optional operation 204, further strain may be imparted 204 after or through the act of inserting the SMP portion 202, thereby straining the SMP portion into an alternate shape. The further strain may be imparted 204, as described further herein, through the act of inserting the SMP portion 202, such as through interaction with a surgical site, and/or through a separate application of mechanical force, such as by using a clamp or hammer. In one embodiment, the further strain may be cumulative to, or added to, the stored strain, and may contain a component in the same direction as the stored strain.

The temperature of the SMP portion is raised 206 to a temperature that causes the SMP portion to activate at a heated activation rate. The temperature of the SMP portion may be raised 206 through heat received from the surgical site (e.g., a patient's body heat). For example, the SMP portion initially have been at a temperature that is below the temperature of the surgical site (e.g., a normal temperature for an exposed portion of the human body during surgery), thus inducing a heat transfer from the surgical site to the SMP portion (e.g., through thermal conduction). The temperature of the SMP portion may alternatively be raised through heat received from another transfer mechanism, including conduction from another material, radiation (e.g., electromagnetic) or other transfer mechanism.

The heated activation rate may be a rate that is significant or insignificant with respect to the surgery and/or installation of the medical device in the surgical site. The temperature to which the SMP portion is raised 206 may be considered an activation temperature for the SMP portion (e.g., causing a threshold amount of shape change to a test sample of the SMP composition while the test sample is largely free of constraints). Because non-zero activation rates occur at temperatures below an activation temperature, even absent constraints, the heated activation rate may occur below what may be considered activation temperature or transition temperature for the SMP material.

The operation 208, a trigger force is applied 208 to the SMP portion. In one embodiment, applying a trigger force 208 follows raising the temperature 206 of the SMP portion. For example, applying the trigger force 208 may increase the activation rate of the SMP portion from the heated activation rate (caused by operation 206) to a faster activation rate.

In another embodiment, the operations 206 and 208 may be reversed in sequence, i.e., applying a trigger force 208 may precede raising the temperature 206 of the SMP. For example, applying the trigger force 208 may activate the SMP at a mechanical activation rate and raising the temperature 206 of the SMP may increase the activation rate of the SMP from the mechanical activation rate to a faster rate.

The temperature of the SMP and trigger forces applied to the SMP may be modified, as described further herein, and the activation rates of the SMP may thereby also be modified. In optional operation 210, the temperature of the SMP may be changed 210 (e.g., through thermal conduction) during the process of installing a medical device comprising the SMP portion. In optional operation 212, the trigger force may be changed 212 (e.g., through using a ratchet mechanism) during the process of installing a medical device comprising the SMP.

Through activation of the SMP (e.g., through raising the temperature, through mechanical activation), as described in operations 206 through 212 (and further herein), a portion of the stored strain in the SMP may be recovered. A determination may be made 214 whether the portion of stored strain has been recovered by the SMP. For example, the portion of stored strain may be a desired portion of strain recovered, thereby transitioning a medical device comprising the SMP portion from a pre-installed configuration to an installed configuration with respect to the surgical site. As another example, the portion of stored strain may be a portion that puts the medical device in a configuration with respect to the surgical site such that the medical device remains in fixed relation to the surgical site while activation from another stimulus (e.g., heat) completes the medical device's transition to the installed configuration.

The stored strain may be determined 214 to have been recovered through observation of the medical device, through instrumentation and/or tools in contact with the medical device, and/or through other means. The SMP portion itself may also be directly tested/observed to make the determination, including through observation/testing of the properties of the SMP portion (e.g., rubbery modulus, stress exerted).

After a portion of the stored strain in the SMP is determined 214 to have been recovered by the SMP, the trigger force may be reduced 216 on the SMP. Reducing the trigger force 216 may comprise an incremental removal of force. Reducing the trigger force 216 may comprise modifying, reducing, and/or ceasing operation of a triggering device applied to the medical device. For example, a clamp may be operated on the medical device to impose a compressive force on the medical device. As another example, a wedge may be operated on or within the implanted medical device to impart or impose an expansive force on the medical device. Triggering elements (e.g., wedge, clamp) and operations thereof are described further herein.

Figure 3:
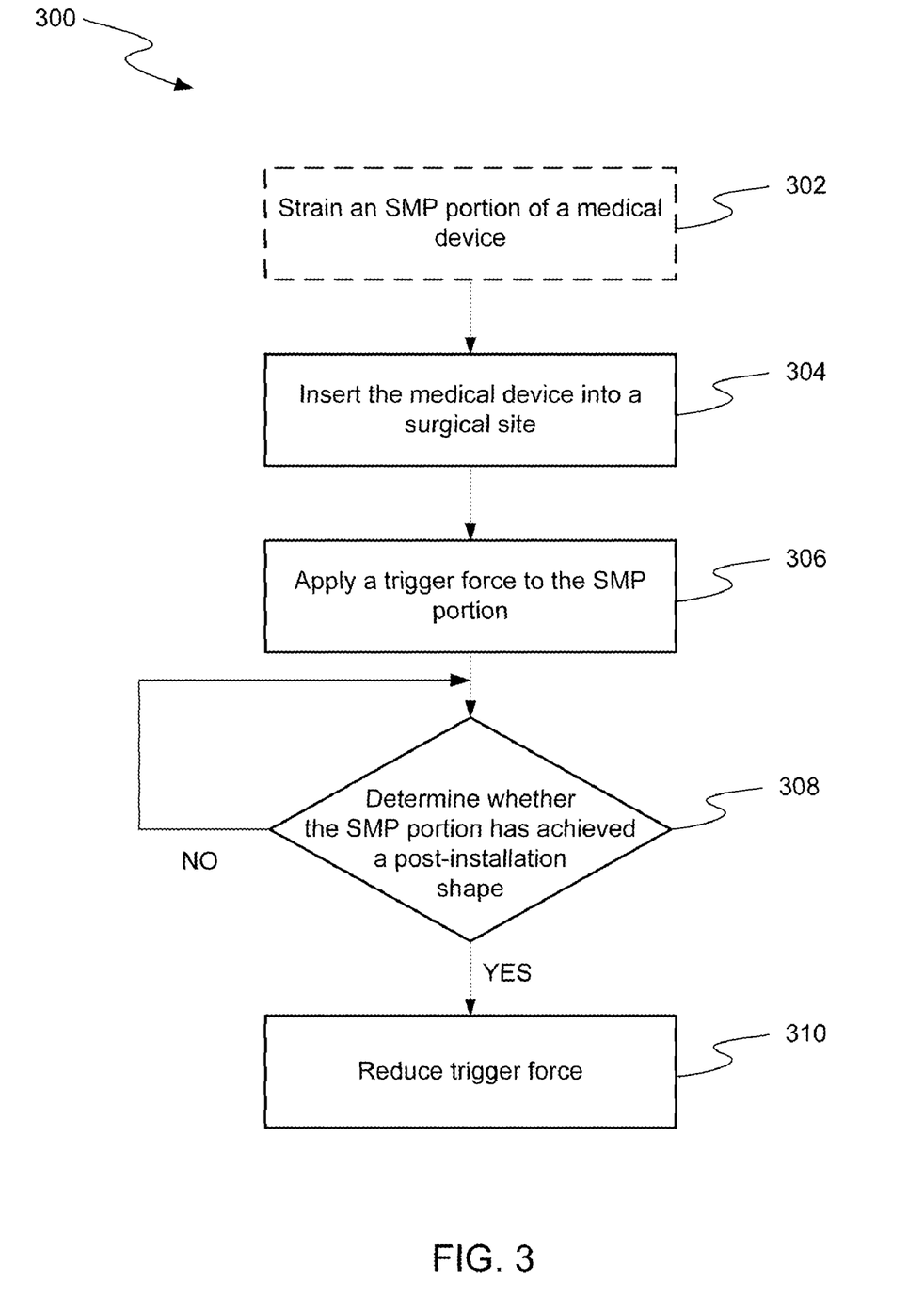
FIG. 3 is a flow chart of another exemplary method for installing a medical device having an SMP portion into a patient's body during surgery.

FIG. 3 shows a flow chart of another embodiment of a method 300 for performing surgery. The method 300 may include the optional operation 302 of straining an SMP portion 302 of a medical device. The straining of an SMP portion 302 and storage of the strain (e.g., a temporary shape of the SMP, a pre-implantation shape) is described further herein. The method 300 includes inserting the medical device 304 into a surgical site, as described further herein.

In some embodiments, applying a trigger force 306 may be performed with, and/or through inserting the medical device 304 into the surgical site. For example, a medical device may interact with the surgical site such that the process of inserting the medical device 304 causes a trigger force to be applied 306. As another example, a trigger force may be applied 306 to an SMP portion of the medical device during the installing of the medical device 304. Examples of devices are described herein (e.g., trigger elements) that may use installation processes whereby trigger forces may be applied 306 during the installation process.

The trigger force applied 306 may include any force on the SMP portion, including compressive, expansive, rotating, shear, tangential, twisting, and/or bending forces. As described further herein, the trigger force applied to the SMP portion does not need to be the same force applied to the medical device. For example, the force applied to the medical device may be a compressive force and the configuration of the medical device may cause an expansive trigger force to be applied 306 to the SMP portion. As another example, the force applied to the medical device may be a torsional or bending force and the configuration of the medical device and/or triggering device may cause expansive trigger forces to one SMP portion and/or compressive trigger forces to another SMP portion. Examples of medical devices that transmit and translate forces applied to the medical device into trigger forces are described further herein.

The trigger force may be applied 306 until it is determined 308, as described further herein, that the SMP has achieved a post-installation shape. The term "post-installation shape" may refer to the shape of the SMP that puts the medical device in an installed configuration with respect to the surgical site. The post-installation shape of the SMP does not need to resemble the installed configuration of the medical device, as other portions of the medical device (e.g., other SMP portions that are non-activated, portions of non-SMP materials) may be configured to translate the change in shape of the SMP to a change in configuration of the medical device as a whole. For example, an expansion of an SMP portion of the medical device may cause other portions of the medical device to flare, tear, extend, and/or rotate.

As described further herein, there may be multiple acceptable installed configurations of the medical device with the surgical site (e.g., multiple different configurations of forces holding a tendon against a bone surface) that may be achieved based on different activation processes. For example, activation of the SMP may continue (e.g., due to thermal activation) after reducing/removing triggering forces from the SMP, thereby potentially transforming the medical device from one installed configuration to another installed configuration. In one embodiment, if the medical device operates to hold a cable member (e.g., tendon, animal soft tissue, cord comprising artificial material) against a bone surface, an installed configuration of the medical device may include a configuration that holds the cable member against a bone surface with a desired level of force. In another embodiment, an installed configuration of a suture anchor achieves a sufficient pull out strength (e.g., minimum force to pull the suture anchor from a bone via an attached suture).

The systems and devices described herein may implement methods described herein. In addition, methods described herein, when implemented in any appropriate medium, including SMPs and other materials, may form systems and devices described herein. Therefore, the descriptions of the methods and systems herein supplement each other and will be understood by those with skill in the art to form a cumulative disclosure.

The methods described herein may be performed by any part of an element of a system described herein. In addition, the methods described herein may be performed iteratively, repeatedly, and/or in parts. In addition, some of the methods or parts of the methods described herein may be performed simultaneously.

Figure 4A:
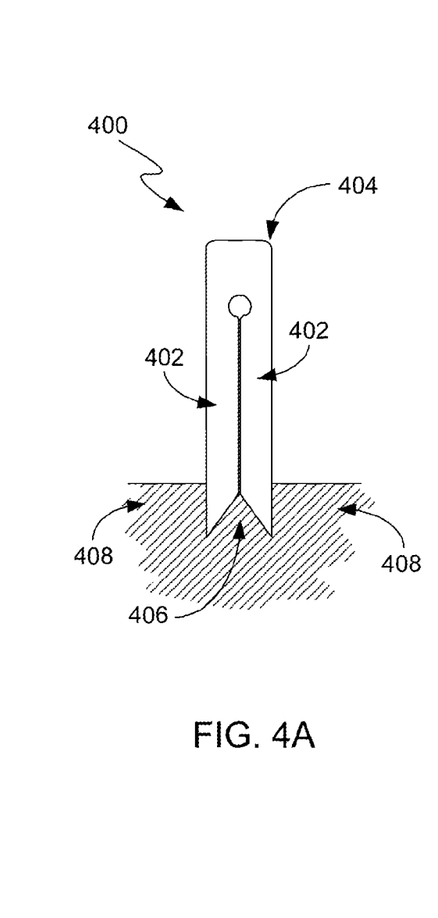
FIGS. 4A-4C are cross-sectional representations of an exemplary suture anchor as it is being installed in a patient's bone through three exemplary stages during installation and configuration change through activation of an SMP portion of the suture anchor.
Figure 4B:
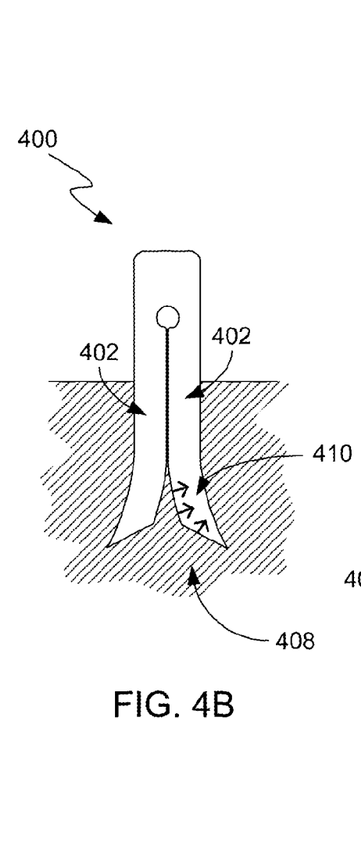
Figure 4C:
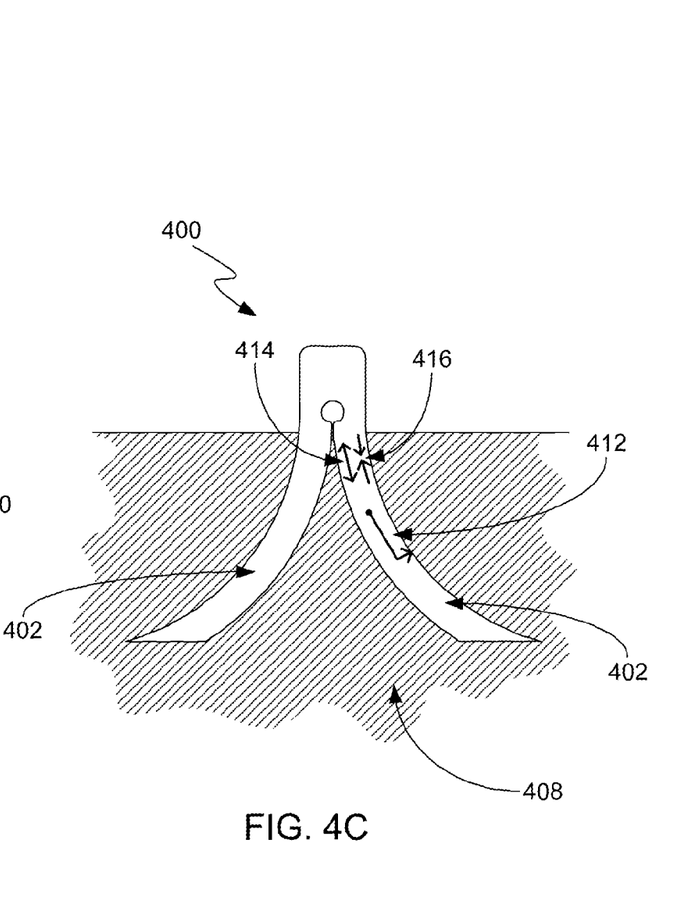

FIGS. 4A-4C are cross-sectional representations of an exemplary suture anchor 400 as it is being installed in a patient's bone 408 through three exemplary stages during installation and configuration change through activation of an SMP portion of the suture anchor. As shown in FIGS. 4A-4C, the installation process of the suture anchor 400 includes a transformation of the configuration of the suture anchor inside the bone 408. The transformation may include an activation of an SMP portion that has complex stored strains, such as stored compressive (negative), expansive (positive), bending, rotating, and twisting strains. The activation of the portion of the SMP may therefore include recovery of these stored strains. In various embodiments, the activation may be performed, as described further herein, through heating the SMP portion, through trigger forces applied to the SMP portion, and/or a combination thereof.

FIG. 4A shows the exemplary suture anchor 400 with an opening 406 that is configured to apply a trigger force to an SMP portion of the suture anchor through insertion of the suture anchor into a bone 408 of a patient. The suture anchor 400 may be made entirely of a single SMP material, although other embodiments may substitute other materials for portions of the suture anchor. As an example, the suture anchor 400 uses an SMP portion that is in a temporary shape before insertion into a patient and is thereafter activated into a different shape, as shown in FIGS. 4B-4C and described further herein. The suture anchor 400 uses an installation process and concomitant interaction with a surgical site to apply a trigger force to the SMP portion.

The elongated body 402 of the suture anchor 400 includes at least a portion made from an SMP material. The embodiment of the suture anchor 400 is made of SMP material and has two elongated bodies 402 substantially aligned while at least one SMP portion is in its temporary shape. The elongated bodies 402 are attached at an attachment portion 404. In one embodiment, the attachment portion 404 is made of SMP material, but the attachment portion does not have stored strain before or after an installation process. In other words, some SMP portions of medical devices need not have the same stored strains as other SMP portions of the medical devices and the interactions of some SMP portions with a surgical site may differ from the interactions of other SMP portions.

In one embodiment, the elongated bodies 402 form an opening 406 that is configured to receive trigger forces when the suture anchor is inserted into the bone 408. The opening 406 may be adapted to receive trigger forces through interfacing directly with the bone 408 and/or may receive trigger forces in another manner, such as through interfacing with another element. Therefore, the opening 406, another element (e.g., wedge element 407), and/or a combination of the opening and another element may be considered a trigger element for the medical device.

In one embodiment, the opening 406 may be configured to engage the bone 408 and receive trigger forces directly from the bone when the ends of the elongated bodies 402 (forming the opening) are inserted in the bone. For example, the opening 406 may be adapted to provide an interface with the bone 408 of a patient whereby the bone presses (e.g., imparts a force) into the opening 406 so as to separate (e.g., strain) the elongated bodies 402.

In another embodiment, a wedge element 407 may be adapted to impart trigger forces to the opening 406 and/or to the elongated bodies 402, and thereby the wedge element 407 may form at least part of a trigger element during several phases of installation of the suture anchor 400 as shown in FIGS. 4A-4C. In one embodiment, the wedge element 407 may be adapted to interact with the suture anchor 400 through translating forces from the bone into forces on the elongated bodies 402 of the suture anchor. In another embodiment, the wedge element 407 may be adapted to be operated through use of a pull cord, as described further herein.

The wedge element 407 may be inserted along with the suture anchor 400 into the bone 408. For example, the wedge element 407 may be attached to the opening 406 of the suture anchor 400, such as through being adhered to the opening, or being formed as part of the same body of material as one or both of the elongated bodies 402. As another example, the wedge element 407 may be adapted to be attached to, adhered to, placed on, or inserted in the bone 408 separately from the opening 406. For example, the wedge element 407 may be adapted to be placed into a pilot hole in the bone 408 before the suture anchor is inserted in the bone.

The wedge element 407 may take another shape than the triangular shape shown in FIGS. 4A-4C. For example, the wedge element 407 may be another shape that aides in translating forces from the bone 408 into trigger forces exerted against portions of the suture anchor 400.

The wedge element 407 may be formed from a portion of the suture anchor 400, and may be adapted to deform during the process of the suture anchor being inserted into the bone 408. For example, the wedge element 407 may be formed as a part of the suture anchor 400 that is adapted to be dislodged from the suture anchor as the suture anchor is inserted into the bone.

FIG. 4B shows the exemplary suture anchor 400 partially inserted into the bone 408 of a patient. As the suture anchor 400 is initially inserted into the bone 408, the opening 406 comes in contact with the patient's bone 408. As the suture anchor continues to be inserted into the bone 408, the bone exerts forces, some of which are shown by arrows 410. The arrows 410 represent some of the normal forces acting on the suture anchor 400 by the bone 408, although there may be other forces acting on the suture anchor while the suture anchor is installed, such as tangential forces (e.g., frictional forces) acting along the surface of the suture anchor.

FIG. 4C shows the exemplary suture anchor 400 inserted into an installed configuration within the bone 408 of a patient. The forces shown by the arrows 410 may be translated into trigger forces applied to at least a SMP portion of the suture anchor 400 containing a stored strain, as described further herein. As shown in FIG. 4C, the trigger forces in the suture anchor 400 may include, in various embodiments, bending moments 412, expansive forces 414, and compressive forces 416. As described further herein, a trigger force is applied to a portion of an SMP with a stored strain such that the SMP is activated to recover that stored strain. For example, an SMP portion with stored strain comprising a shear strain (e.g., twist) may be activated to a trigger force with an opposing bending moment 412. Other interactions between stored strains in SMP portions and their activation via trigger forces are described further herein.

An SMP with complex stored strains, which is described further herein, may be activated by complex trigger forces. Therefore, some or all of the trigger forces shown in FIG. 4C, including bending moments 412, expansive forces 414, and compressive forces 416 may be applied to an SMP portion of the suture anchor 400. In other embodiments, other trigger forces may be applied to the suture anchor 400 to activate other stored strains in the suture anchor.

Figure 5A:
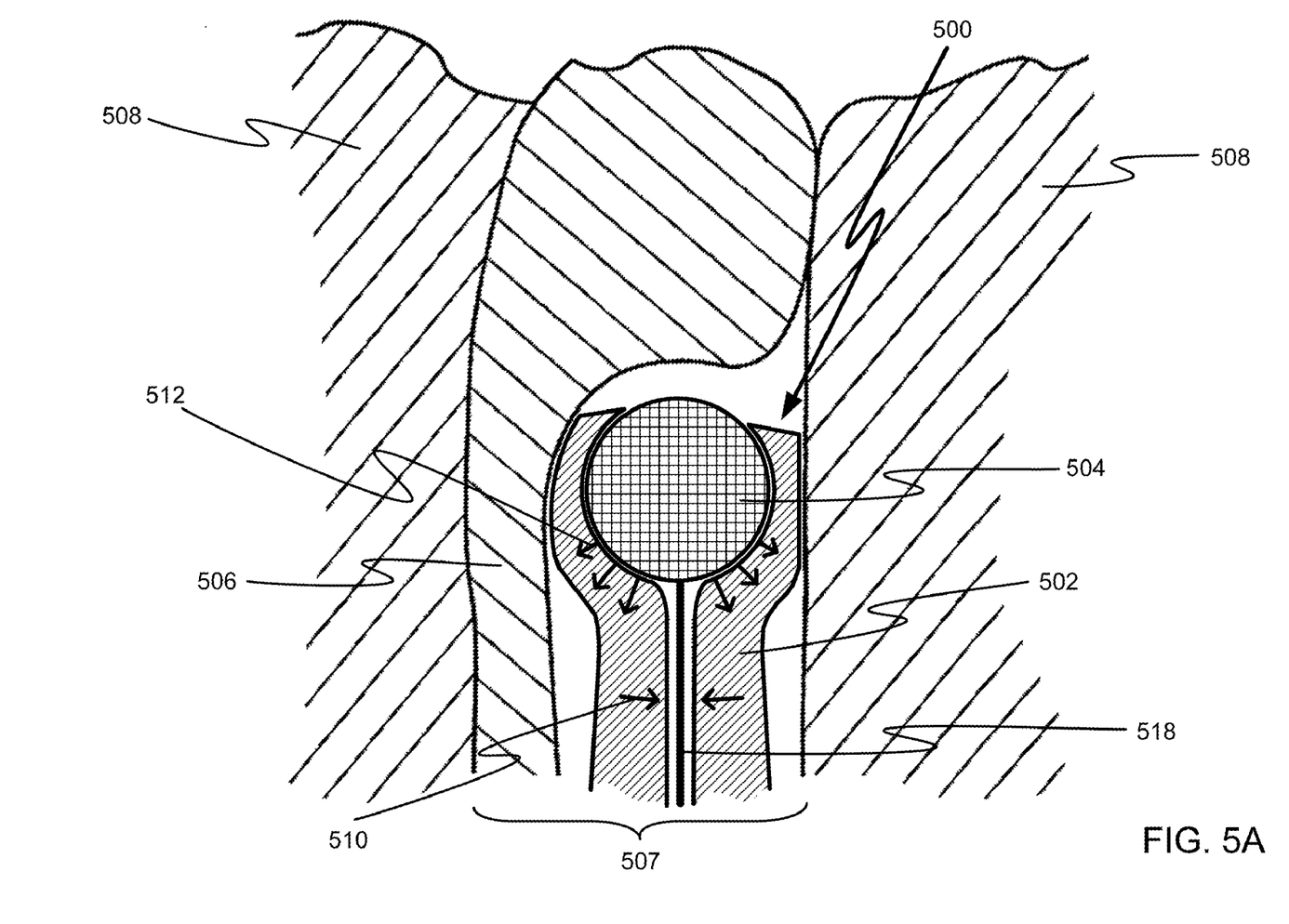
FIGS. 5A-5B are cross-sectional representations of an exemplary cylindrical medical device with a wedge element through two exemplary stages of installation through activation of an SMP portion while in a surgical site in a patient's bone.
Figure 5B:
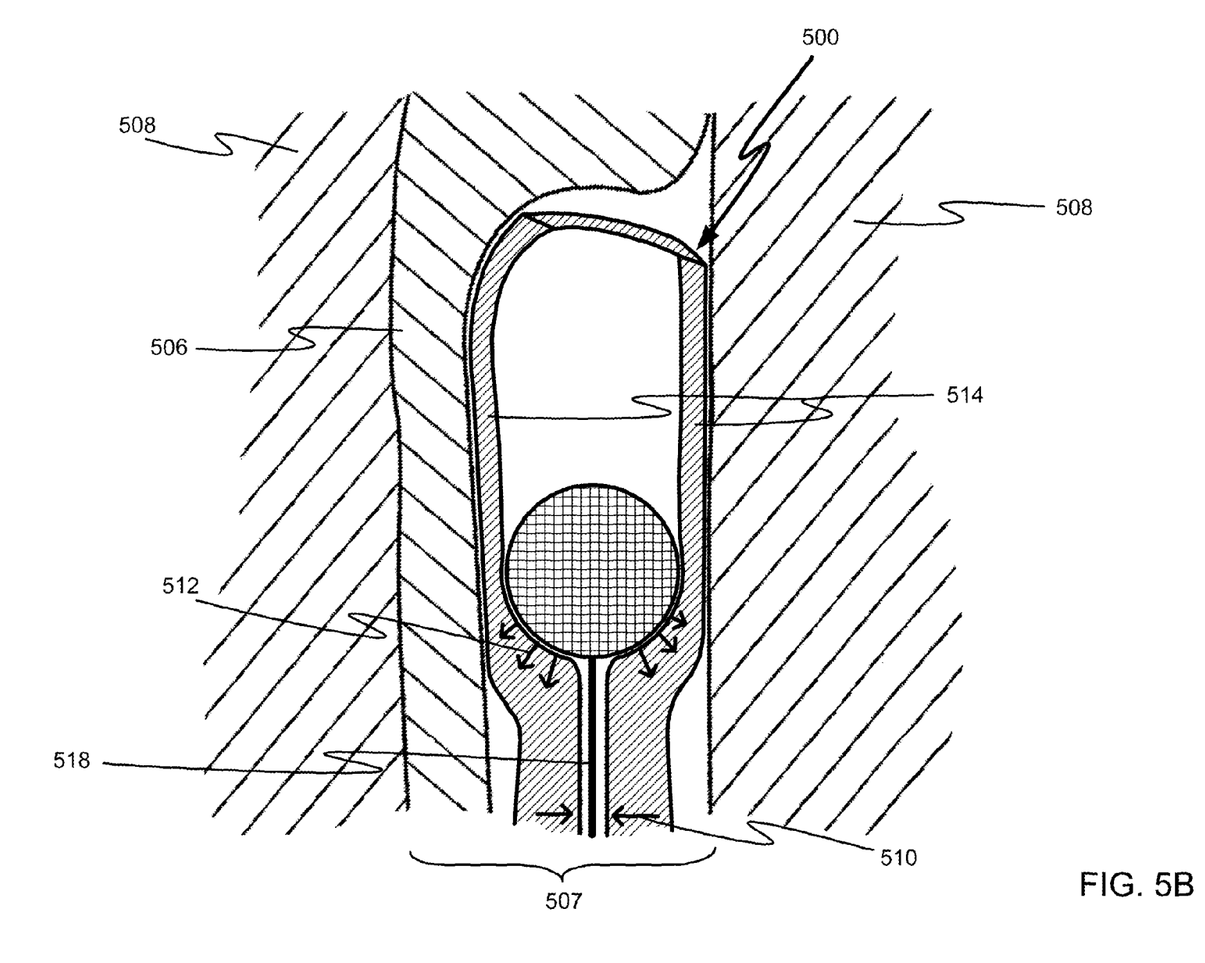

FIGS. 5A-5B are cross-sectional representations of an exemplary cylindrical medical device 500 with a wedge element 504 through two exemplary stages of installation through activation of an SMP portion while the medical device is in a surgical site in a patient's bone. The medical device 500 may be installed within a surgical site such as a bone cavity 507 defined in bone 508 to press a cable member 506 such as a tendon or artificial tendon replacement against the bone cavity. In the installed configuration, the medical device 500 is expanded against the walls of the bone cavity 508 and forces between and among the medical device, cable member 506, and the bone 508 to hold them in spatial relation to one another. In some embodiments, the cable member 506 may be used as a replacement tendon attached to a bone 508 of a patient. For example, in an anterior cruciate ligament repair surgery, a cable member may be attached to the distal end of a patient's femur and attached to the proximal end of the patient's tibia inside the patient's knee.

FIG. 5A shows the medical device 500 with the wedge element 504 pressing against the end of the body 502 of the medical device. In one embodiment, there is an SMP portion of the body 502 with a stored strain, such as a stored compressive circumferential strain 510. The wedge element 504 is adapted to impart expansive trigger forces (indicated by the expansive arrows 512) to activate the stored strain (indicated by the compressive arrows 510) in the SMP portion. The wedge element may be operated through a pull cord 518, through direct operation (e.g., hammering, driving), or through other means. Wedge element 504 may be formed in many shapes, including spherical (as shown), ellipsoid, angled, pyramid.

A pull cord 518 may be designed to respond to an anticipated stress (e.g., pulling on a long axis of the pull cord) through straining to an anticipated amount of strain. The strain in the pull cord 518 may be adapted to be used to apply forces and/or to recover that strain through a process that beneficial to the installation of the medical device (e.g., application of forces to the wedge element 504). For example, the pull cord 518 may be fixed against a part of the medical device 500 (e.g., through the use of a ratchet mechanism), such as an end of the medical device, after applying a force to the pull cord (e.g., operation of the wedge element via applying the force to the pull cord), and the pull cord may thereafter apply a force to the wedge element 504 through recovery of strain in the pull cord. A pull cord 518 may also recover strain while the pull cord is being used to operate the wedge element (e.g., during reductions in stress on the pull cord).

A pull cord 518 may be designed to be significantly strained (e.g., stretched) along its long axis under the stress anticipated to be used in operating the wedge element 504 in the medical device. A pull cord 518 may be designed such that the pull cord will respond elastically under the stress anticipated to be used in operating the wedge element 504. A pull cord 518 may be made of a material (e.g., elastic material, shape memory alloy) such that significant strain may be stored in the pull cord without plastic deformation and such that the pull cord may apply forces to the wedge element based on the stored strain in the pull cord. For example, in one embodiment, the pull cord 518 may be made of a stainless steel wire that is designed (e.g., sufficiently thick) as to avoid the pull cord from being plastically deformed. In another embodiment, the pull cord 518 may be designed as a structure other than a solid longitudinal cord (e.g., a spring) in order to tailor the force-displacement response of the pull cord.

In one embodiment, a pull cord 518 may be made of a shape memory alloy and designed to undergo a phase transformation from an austenitic to a martensitic phase in at least part of the shape memory alloy under the stress anticipated to be used in operating the wedge element 504. For example, a pull cord 518 made at least in part of shape memory alloy may be designed to be strained by the stress anticipated in operating the wedge element 504, and the pull cord may apply forces to the wedge element through the recovery of that strain. The shape memory alloy in the pull cord 518 may exhibit "superelastic" or "pseudo-elastic" properties based on a martensitic phase present in the shape memory alloy, and the forces applied by the pull cord 518 through the recovery of the strain in the martensitic phase may be relatively constant, as compared to elastic recovery of strain by the same material in its austenitic phase.

FIG. 5B shows the medical device 500 with the wedge element 504 partially translated through the body 502. The configuration of the medical device 500 is shown in FIG. 5B in one of potentially multiple installed configurations of the medical device, as described further herein. In the installed configuration shown, a part 514 of the medical device body 502 containing an SMP portion in an installed shape holds the combination of the medical device 500, the cable member 506, and the bone 508 in spatial relation to one another. Activation may continue, as described further herein, through, for example, continued thermal activation (e.g., interaction with the surgical site), and/or continued constraint provided by the wedge element 504. The wedge element 504 may be adapted to continue to provide constraint(s) and/or trigger force(s) due to its continued presence within the body 502 after ceasing operation of the wedge element (e.g., through pull cord 518, through hammering the wedge element directly).

Figure 6A:
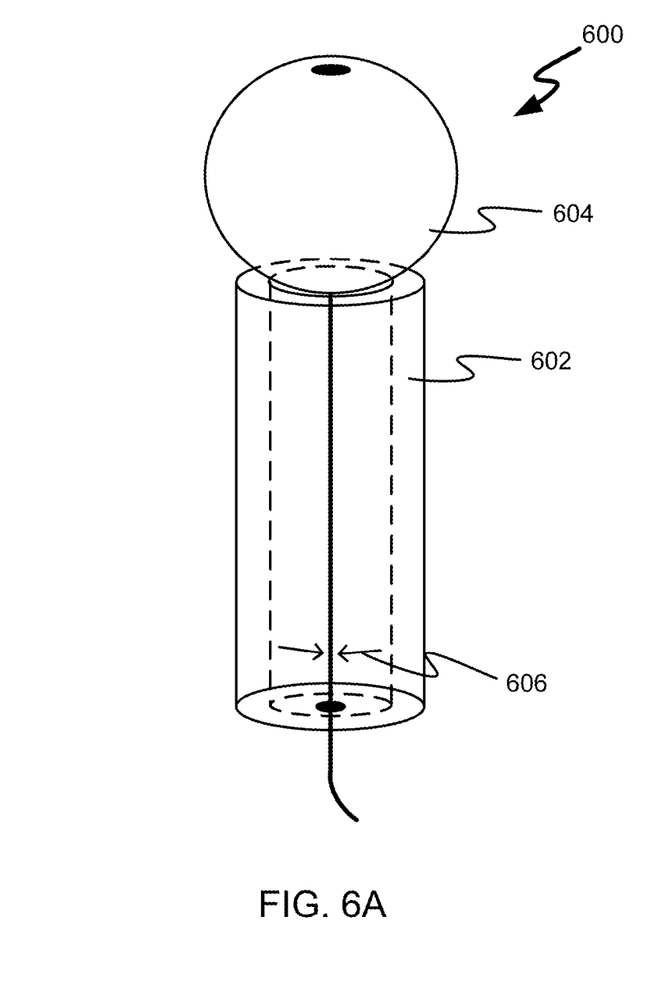
FIGS. 6A-6B are representations of an exemplary cylindrical medical device with a wedge element through two exemplary stages of activation of an SMP portion while in an unconstrained environment (substantially free of constraints).
Figure 6B:
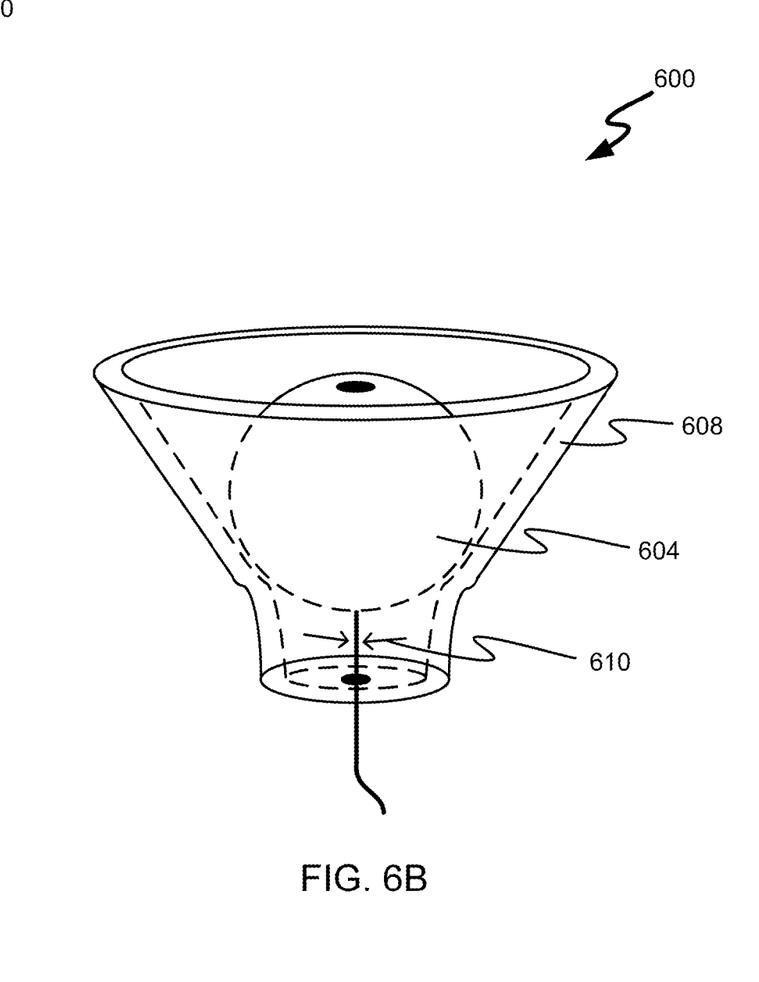

FIGS. 6A-6B are representations of an exemplary cylindrical medical device 600 with a wedge element 604 through two exemplary stages of activation of an SMP portion while in an unconstrained environment (substantially free of constraints).

FIG. 6A shows the exemplary medical device 600 in a position with stored strain in the device 606 and a wedge element 604 adapted to be coupled the body 602 of the device. The configuration of the medical device 600 shown in FIG. 6A may be an exemplary storage configuration of the device, such as a configuration in which the device may be shipped or stored prior to use in surgery.

FIG. 6B shows the exemplary medical device 600 in a position with a partially activated part 608 of the medical device that has recovered some or all of the stored strain 610, as described further herein. The exemplary medical device 600 shown in FIG. 6B may have been activated through both the operation of the wedge element 604 and through another activation stimulus (e.g., temperature), thereby allowing the top portion of the medical device to recover strain beyond the strain recovered through activation caused by operation of the wedge element 604 alone.

The medical device 600 has been activated in an unconstrained environment and allowed to change shape while reaching force equilibria (e.g., substantially zero force, gravitational force) with its environment that are different equilibria than reached by a medical device that is activated inside a surgical site. During activation in a constrained environment, as described further herein and with respect to FIGS. 5A-5B, strains may remain in portions of the medical device due to force equilibria met between the medical device and its environment (e.g., cable member, bone) despite sufficient time for activation to allow strain recovery to occur through the respective activation rates of the portions of the medical device. During activation of the medical device 600, different portions of the medical device may have different respective activation rates, as described further herein. In the configuration shown in FIG. 6B, stored strains 610 may remain in portions apart from the top portion and be unrecovered due to the different activation rates.

Figure 7:
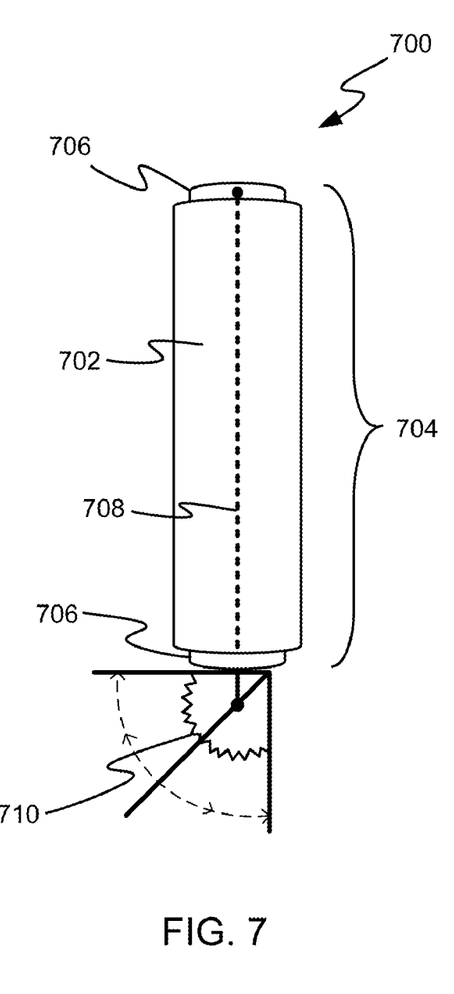
FIG. 7 is a schematic of an exemplary medical device with a compressive trigger element partially disposed within the medical device.

FIG. 7 shows an embodiment of a medical device 700 with a compressive trigger element 704. The compressive trigger element 704 includes two end plates 706 situated on opposite ends of the body 702 of the medical device 700. The end plates 706 are attached through a pull cord 708 which is actuated by ratchet mechanism 710. The ratchet mechanism 710 presses an end plate 706 against an end of the body 702, while holding the pull cord 708 in relation to the both end plates 706. The ratchet mechanism 710 may be used to apply, as described further herein, a series of discreet compressive constraints on the body 702 of the medical device 700 through pulling the pull cord 708. The ratchet mechanism 710 may be used to apply leverage to the pull cord 708 and/or to latch the pull cord, thereby aiding operation of the pull cord.

An SMP portion of the medical device 700 may be strained, activated, and otherwise operated as described further herein. In one embodiment, the medical device 700 may be inserted into a surgical site with a stored strain that is adapted to be activated by a trigger force as described further herein from the trigger element 704.

In one embodiment, the medical device 700 may be used in a surgery fixing a bone cavity and a cable member, as described further herein. Portions of the trigger element 704 may be configured to remain within the patient. For example, the pull cord 708 and/or either or both the end plates 706 may remain within the patient with the medical device 700 in the surgical site. Other portions of the medical device 700 and/or elements related to the trigger element 704 (e.g., the ratchet mechanism 710) may be configured to be removed from the surgical site during the surgical procedure.

Figure 8:
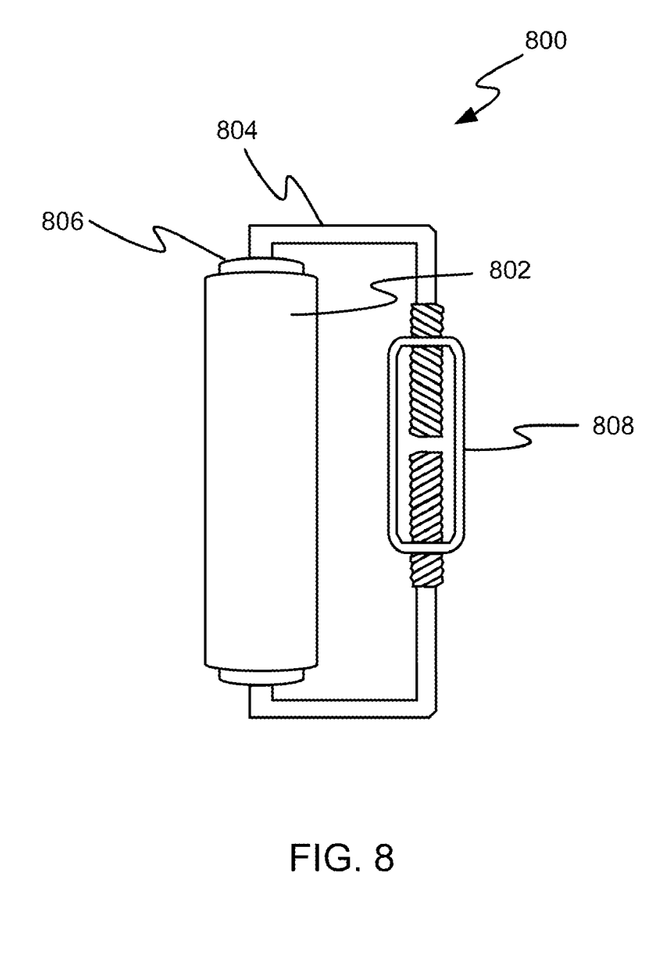
FIG. 8 is a schematic of another exemplary medical device with a compressive trigger element entirely disposed outside of the medical device.

FIG. 8 shows another embodiment of a medical device 800 with a compressive trigger element 804. The compressive trigger element 804 contains two end plates 806 situated on opposite ends of the body 802 of the medical device 800. The end plates 806 are attached to each other through a clamp mechanism 808 situated around the body 802. The clamp mechanism 808 may actuate the end plates 806 to apply a compressive constraint to the body 802 of the medical device 800. The clamp mechanism 808 may be configured to apply constraints to the body 802 continuously, discreetly, and/or a combination thereof.

The medical device 800 may be used in a surgery fixing the medical device and a cable member in relation to a bone cavity, as described further herein. In one embodiment, the clamp mechanism 808 may be integrated with the medical device 800 and/or may remain within the patient after the surgical procedure is complete. In another embodiment, the clamp mechanism 808 may be removed from the patient before the surgical procedure is complete. For example, the clamp mechanism 808 may be configured to access the medical device 800 through two ends of a bone cavity, such as at either end of a bone tunnel through the distal end of a patient's femur.

Other embodiments of devices may include devices that utilize a stored twisting, bending, expansive and/or compressive strain in an SMP portion, as described further herein. A trigger force that activates the stored strain may allow the strain to recover into a different (e.g., post-installation) shape, thereby causing transformation of an associated medical device into an installed configuration, as described further herein. The specific devices described herein are examples of the broad range of potential configurations of devices described herein through, for example, the description of the operations of the materials of the devices. Therefore, the description herein of devices and methods should serve as illustrative examples from which teachings may be drawn for further useful devices.

What is claimed is:

1. A surgical method comprising the steps of:
    (A) inserting a medical device into a surgical site;
        (i) wherein the medical device contains a shape memory polymer portion that has been set with a stored strain between a temporary shape and a memorized shape;
        (ii) wherein the inserting is performed at a first temperature below an activation temperature of the shape memory polymer;
    (B) activating the shape memory polymer portion via applying a physical force with an activation triggering element in an opposing direction to the stored strain at a second temperature below the activation temperature; and
    (C) recovering a portion of the stored strain as the shape memory polymer potion moves from the temporary shape toward the memorized shape at a third temperature below the activation temperature via the activating step.

2. The method of claim 1, further comprising:
completing recovery of the stored strain while the shape memory polymer portion remains below the activation temperature.

3. The method of claim 1, wherein the first temperature is different from the second temperature.

4. The method of claim 1, wherein the first temperature is different from the third temperature.

5. The method of claim 1, wherein the second temperature is different from the third temperature.

6. The method of claim 1, wherein the first temperature is different from the second temperature, and wherein the second temperature is different from the third temperature.

* * * * *

UNITED STATES PATENT AND TRADEMARK OFFICE
CERTIFICATE OF CORRECTION

| | |
|---|---|
| PATENT NO. | : 8,069,858 B2 |
| APPLICATION NO. | : 12/960276 |
| DATED | : December 6, 2011 |
| INVENTOR(S) | : Kenneth A. Gall |

It is certified that error appears in the above-identified patent and that said Letters Patent is hereby corrected as shown below:

Column 16, line 44 in claim 1: replace "potion" with "portion".

Signed and Sealed this
Thirty-first Day of January, 2012

David J. Kappos
*Director of the United States Patent and Trademark Office*